United States Patent
Bhat et al.

(10) Patent No.: US 10,931,859 B2
(45) Date of Patent: Feb. 23, 2021

(54) LIGHT EMITTER AND SENSORS FOR DETECTING BIOLOGIC CHARACTERISTICS

(71) Applicant: InSyte Systems, Newark, CA (US)

(72) Inventors: Jerome Chandra Bhat, Palo Alto, CA (US); Richard Ian Olsen, Truckee, CA (US)

(73) Assignee: InSyte Systems, Newark, CA (US)

( * ) Notice: Subject to any disclaimer, the term of this patent is extended or adjusted under 35 U.S.C. 154(b) by 162 days.

(21) Appl. No.: 15/600,480

(22) Filed: May 19, 2017

(65) Prior Publication Data

US 2017/0337412 A1    Nov. 23, 2017

Related U.S. Application Data

(60) Provisional application No. 62/340,218, filed on May 23, 2016.

(51) Int. Cl.
*H04N 5/225* (2006.01)
*A61B 5/1172* (2016.01)
*G06K 9/00* (2006.01)

(52) U.S. Cl.
CPC ......... *H04N 5/2256* (2013.01); *A61B 5/1172* (2013.01); *G06K 9/0004* (2013.01);
(Continued)

(58) Field of Classification Search
CPC .... G06K 2009/00932–00939; G06K 9/00892; G06K 9/00006; G06K 9/00013;
(Continued)

(56) References Cited

U.S. PATENT DOCUMENTS 7,177,451 B2   2/2007   Higuchi
7,876,929 B2   1/2011   Matsumura et al.
(Continued)

FOREIGN PATENT DOCUMENTS

EP   2131322 A1   12/2009
EP   2983109 A1   2/2016
(Continued)

OTHER PUBLICATIONS

PCT/US2017/033859 filed May 22, 2017, "International Search Report and Written Opinion" dated Aug. 14, 2017, 10 pages.

*Primary Examiner* — Michael S Osinski
(74) *Attorney, Agent, or Firm* — Patent Law Group; Brian D. Ogonowsky (57) ABSTRACT

A bio-sensor device includes a surface for touching by a body part, such as a finger. A light source, such as an array of LEDs, emit light through the surface so as to be reflected and partially absorbed by the body part An array of photodetectors detects light reflected back by the body part and generates signals corresponding to an image of the light reflection, which corresponds to the light absorption pattern in the body part. The light absorption pattern may correlate to a fingerprint, a blood vessel pattern, blood movement within the blood vessels, or other biometric feature. A processor receives the signals from the photodetectors and analyzes the signals to determine a characteristic of the body part. The characteristic may be used to authenticate the user of the bio-sensor device by comparing the detected characteristic to a stored characteristic.

16 Claims, 5 Drawing Sheets

(52) U.S. Cl.
CPC .............. *A61B 2562/0233* (2013.01); *G06K 2009/00932* (2013.01); *G06K 2009/00939* (2013.01)

(58) Field of Classification Search
CPC .... G06K 9/0002–0008; G06K 9/00107–0012; G06K 9/00885; G06K 9/2018; G06K 9/00067; G06K 9/00496; A61B 5/1172; A61B 5/489; A61B 5/117; A61B 5/6826; A61B 5/0261; G06F 3/044; G06F 21/32; G06F 21/83; G06T 7/0002–0012
See application file for complete search history.

(56) References Cited

U.S. PATENT DOCUMENTS

| | | | | |
|---|---|---|---|---|
| 7,961,918 | B2* | 6/2011 | Hikita | G06K 9/0002 |
| | | | | 382/115 |
| 8,787,624 | B2* | 7/2014 | Hama | G06K 9/036 |
| | | | | 382/115 |
| 8,923,573 | B2 | 12/2014 | Shinzaki | |
| 9,020,226 | B2* | 4/2015 | Kamei | A61B 5/117 |
| | | | | 382/128 |
| 9,195,900 | B2* | 11/2015 | Gu | G06K 9/46 |
| 9,466,653 | B2 | 10/2016 | de Jong et al. | |
| 9,570,002 | B2 | 2/2017 | Sakariya et al. | |
| 10,140,536 | B2* | 11/2018 | Hung | G06K 9/00892 |
| 2003/0044051 | A1 | 3/2003 | Fujieda | |
| 2003/0090650 | A1 | 5/2003 | Fujieda | |
| 2004/0208346 | A1 | 10/2004 | Baharav et al. | |
| 2005/0123176 | A1 | 6/2005 | Ishii et al. | |
| 2005/0237317 | A1 | 10/2005 | Cok | |
| 2006/0098848 | A1* | 5/2006 | Nagasaka | A61B 5/1172 |
| | | | | 382/124 |
| 2006/0115128 | A1 | 6/2006 | Mainguet | G06K 9/00026 |
| | | | | 382/115 |
| 2007/0036399 | A1* | 2/2007 | Matsumura | A61B 5/1172 |
| | | | | 382/124 |
| 2007/0041005 | A1* | 2/2007 | Song | G06K 9/0004 |
| | | | | 356/71 |
| 2007/0253607 | A1 | 11/2007 | Higuchi | |
| 2008/0008365 | A1* | 1/2008 | Hikita | G06K 9/0002 |
| | | | | 382/124 |
| 2008/0232653 | A1* | 9/2008 | Rowe | A61B 5/0059 |
| | | | | 382/124 |
| 2008/0317303 | A1 | 12/2008 | Konno et al. | |
| 2009/0039241 | A1 | 2/2009 | Ueki | |
| 2009/0074255 | A1 | 3/2009 | Holm | |
| 2009/0074263 | A1* | 3/2009 | Higuchi | A61B 5/1172 |
| | | | | 382/126 |
| 2009/0245591 | A1* | 10/2009 | Rowe | G06K 9/00033 |
| | | | | 382/115 |
| 2010/0008545 | A1* | 1/2010 | Ueki | G06K 9/00033 |
| | | | | 382/115 |
| 2010/0164906 | A1 | 7/2010 | Fukunaga et al. | |
| 2010/0283765 | A1 | 11/2010 | Gotoh et al. | |
| 2011/0007951 | A1* | 1/2011 | Mil'shtein | G06K 9/00033 |
| | | | | 382/124 |
| 2011/0187653 | A1* | 8/2011 | Ko | G06F 3/0412 |
| | | | | 345/173 |
| 2011/0187679 | A1 | 8/2011 | Ko | |
| 2011/0200237 | A1* | 8/2011 | Nakamura | A61B 5/1171 |
| | | | | 382/127 |
| 2012/0194662 | A1* | 8/2012 | Zhang | G06K 9/2018 |
| | | | | 348/77 |
| 2013/0129164 | A1* | 5/2013 | Gu | G06K 9/00013 |
| | | | | 382/124 |
| 2013/0136327 | A1* | 5/2013 | Kamei | A61B 5/117 |
| | | | | 328/128 |
| 2014/0028575 | A1* | 1/2014 | Parivar | G06F 3/0414 |
| | | | | 345/173 |
| 2014/0354597 | A1 | 12/2014 | Kitchens et al. | |
| 2015/0146944 | A1* | 5/2015 | Pi | H04L 63/0861 |
| | | | | 382/124 |
| 2015/0193669 | A1* | 7/2015 | Gu | G06K 9/46 |
| | | | | 348/77 |
| 2015/0346856 | A1 | 12/2015 | Wassvik | |
| 2015/0363632 | A1 | 12/2015 | Ann et al. | |
| 2015/0364107 | A1 | 12/2015 | Sakariya | |
| 2016/0042219 | A1 | 2/2016 | Bae et al. | |
| 2016/0092717 | A1 | 3/2016 | Ling | |
| 2016/0132712 | A1* | 5/2016 | Yang | G06K 9/0002 |
| | | | | 348/77 |
| 2016/0239151 | A1 | 8/2016 | Sun et al. | |
| 2016/0342282 | A1 | 11/2016 | Wassvik | |
| 2017/0020841 | A1 | 1/2017 | Ishida et al. | |
| 2017/0076133 | A1 | 3/2017 | Hillmann et al. | |
| 2017/0220841 | A1 | 8/2017 | Maeda et al. | |
| 2017/0228125 | A1 | 8/2017 | Lee et al. | |
| 2018/0211085 | A1* | 7/2018 | Liu | G02F 1/13306 |
| 2018/0267651 | A1 | 9/2018 | Park | |
| 2018/0322325 | A1 | 11/2018 | Lee et al. | |
| 2019/0033976 | A1 | 1/2019 | Cao et al. | |

FOREIGN PATENT DOCUMENTS

| | | |
|---|---|---|
| JP | 2003146107 A | 5/2003 |
| JP | 2008212311 A | 9/2008 |
| JP | 2008308037 A | 12/2008 |
| JP | 2009003821 A | 1/2009 |
| JP | 2010131180 A | 6/2010 |
| JP | 2016038913 A | 3/2016 |

* cited by examiner

LIGHT EMITTER AND SENSORS FOR DETECTING BIOLOGIC CHARACTERISTICS

CROSS-REFERENCE TO RELATED APPLICATIONS

This application is based on and claims priority from U.S. provisional patent application Ser. No. 62/340,218, filed on May 23, 2016, by Jerome Chandra Bhat and Richard Ian Olsen, assigned to the present assignee and incorporated herein by reference.

FIELD OF THE INVENTION

This invention relates to the sensing of biologic characteristics, such as blood flow, blood components, fingerprints, blood vessel patterns, etc. and, in particular, to the sensing of such characteristics using light and photodetectors.

BACKGROUND

It is known that applying light of particular wavelengths (e.g., red or IR) to a human body part (e.g., a finger) and measuring the light transmitted through the body part can be used to detect blood flow (e.g., a pulse), components in the blood (such as hemoglobin), fat, and other characteristics. Generally, the light absorption correlates to particular characteristics.

However, such systems are generally limited to medical devices performing only a single function. Further, since the measurement of light absorption is through the body part, the device must be specifically made to surround the particular body part being tested, such as a finger.

What is needed is a more flexible and compact biologic sensor that can be used for a variety of functions and can be used for medical as well as non-medical purposes, such as authentication. For user authentication, the biologic sensor should be able to be easily integrated into existing consumer products.

SUMMARY

An integrated and compact light emitter and sensor device is described that can be used to detect biologic characteristics of the person using the device. The characteristics can be used for medical/diagnostic purposes as well as authentication of the person. For example, the device may be installed in a smart phone or a computer to authenticate the user.

In one embodiment, high resolution pixels formed by multi-wavelength light sources, such as LEDs or filtered white light, provide light that penetrates a body part, such as a finger, when applied to the skin. An array of photodetectors is integrated in the light emitter and detects the magnitude of light reflected back from the body part, where the magnitude of the light reflected back is affected by absorption of the light by the body part. The array of photodetectors may create a high resolution image of the light absorption. The pixels (e.g., wavelengths) may be controlled to target certain biologic characteristics, and the resolution of the device may be high to detect detailed characteristics, such as fingerprints and blood vessel patterns. A video image may even be captured. Optics may be used to detect the absorption only at a certain depth into the skin. A processor in the device may be programmed to analyze the signals from the photodetectors and generate results, such as authentication of the user.

The devices may be compact and inexpensive, allowing their use in portable devices for authentication or for an analysis of the user's biologic characteristics.

Various other designs and uses of such devices are described.

BRIEF DESCRIPTIONS OF DRAWINGS

Elements that are the same or equivalent in the various figures are labeled with the same numeral.

DETAILED DESCRIPTION

Various types of bio-sensor devices are described that emit light of certain wavelengths and detect, using image capture, the absorption of the light by a person's body in contact with the light emission window. Other uses are described.

Figure 1:
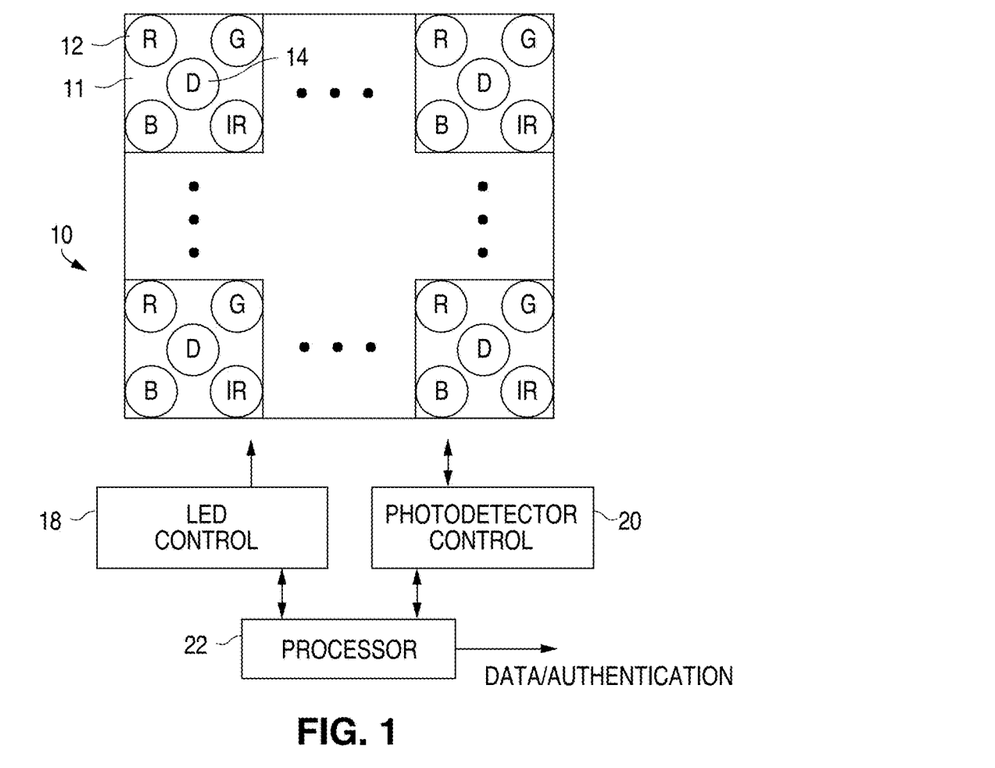
FIG. 1 is a top down view of a high resolution light emitter that may emit selected wavelengths of light in selected areas, where the device also include an array of photodetectors within each multi-wavelength pixel area to sense light absorption from a person's body part contacting the light emitting surface.

FIG. 1 is a top down view of a bio-sensor device 10 having a size suitable for the image to be captured. In one embodiment, the device 10 is only large enough to detect a finger touching its surface.

The device 10 comprises an array of pixels 11 formed by micro-LEDs 12 or other light sources, such as vertical-cavity surface emitting lasers (VCSELs). Such lasers are considered a subset of light emitting diodes. The LEDs 12 may be different kinds that emit different peak wavelengths of interest, or the LEDs 12 may be the same kind (e.g., UV LEDs) with different phosphors to emit the different wavelengths of interest. In the example shown, the LEDs 12 in a single pixel 11 include red R, blue B, green G, and IR-emitting LEDs. Different wavelengths penetrate the skin by different amounts; shorter wavelengths (blue, green) penetrating less deeply into the skin than longer wavelengths (red, infrared). In another embodiment, the device 10 is only intended for a particular function, such as detecting blood flow in a finger, and the LEDs 12 only emit a single narrow band of wavelengths for the particular function, such as red or IR. Each pixel 11 also includes a broadband photodiode 14 or other type of photodetector. LEDs 12 emitting different wavelengths may be separately energized, so the output of the photodiodes 14 can be correlated to the wavelength emitted by the energized LEDs 12. The resolution of the device 10 may be the same as a high resolution television.

LEDs of any one wavelength from within the pixel array may also optionally be sequentially illuminated, with one or more detectors from within the pixel array concurrently being read, to eliminate cross-talk so as to enable further enhancement of the resolution of the image obtained by digital processing. For example, such sequentially illumination enables enhanced distinguishing of the location of absorbing features (e.g., blood vessels) within the body part from locations which are merely scattering but not absorbing the light. Additionally, the detector(s) being read may only be those proximate to the illuminated LED so that the sampled body part area is highly localized.

The LEDs may be OLEDs or inorganic LEDs.

Alternatively, the various color pixels may be formed by a liquid crystal display (LCD). A typical LCD uses a white light backlight having a broad range of wavelengths. Color filters, such as red, green, blue, and IR filters, form sub-pixels and are positioned behind a controllable liquid crystal layer. The liquid crystal layer effectively has a light shutter for each sub-pixel location. By controlling the light shutters, the different colors in each pixel are controlled. The photodiodes 14 may then be formed in a transparent laminated layer over the top of the LCD.

In either embodiment, the photodiodes 14 and light emitting pixels are on the same side of the person's body part to be analyzed, so that the photodiodes 14 detect an image of the reflected light, such as for detecting the absorption of light by the person's skin. This is in contrast to known devices that detect the amount of light that passes through a person's body part. The image of the reflected light corresponds to an image of absorbed light, since localized absorption in the body part being detected is basically determined by detecting differences between the reflected light received by different photodiodes 14. Such differences can be used to map the absorption pattern and compare it to a stored absorption pattern. Accordingly, the absolute magnitudes of the reflected light may vary based on the body part being sampled, any ambient light, current to the LEDs, etc., but the differences in the light reflection magnitudes will still correspond to the absorption pattern within the body part.

An example of an array of pixels 11 for a combination fingerprint detector and blood vessel location detector may be an array that is 2 cm×2 cm and contains 800 pixels 11. The resolution may be as little as 0.25 mm. Such an array size can be incorporated in a smartphone or other handheld device for authentication of the user using two different tests.

An LED controller 18 controls the energization of the LEDs 12 using, for example, row and column addressing, and the photodiodes 14 are controlled by a photodetector controller 20. A processor 22 provides overall control of the controllers 18 and 20 and detects the outputs of the various photodiodes 14 for further processing, depending on the desired function. In one embodiment, the processor 22 controls the device to detect a fingerprint as well as the location of blood vessels in the finger, a pulse, and components in the blood. Multiple images may be obtained, like a video, for analyzing blood flow. The processor 22 may compare the data to stored information in a memory for authenticating the user or may use the data for medical analysis.

In one embodiment, the LED controller 18 rasters or otherwise spatially sequences the illumination of the LEDs whilst the photodetector controller 20 captures a sequence of images corresponding to the multiple distinct illumination states. The processor 22 may process the sequence of data to compensate the captured images for scattered light, thereby increasing the resolution of the combined image formed by absorbing features within the body part in contact with the device.

The entire device 10, including the processor 22 and controllers 18/20, may be formed as a single modular device that only requires power leads and data leads.

Different sections of the pixel array, or ones of the pixels 11, may be separately energized to reduce cross-talk between photodiodes 14 and LEDs 12 from different pixels 11. Ideally, the body part is in direct contact with the device 10 for minimizing scattering of the impinging and reflected light to obtain the highest resolution image. Focusing and directional optics may also be used to further improve resolution.

Figure 2:
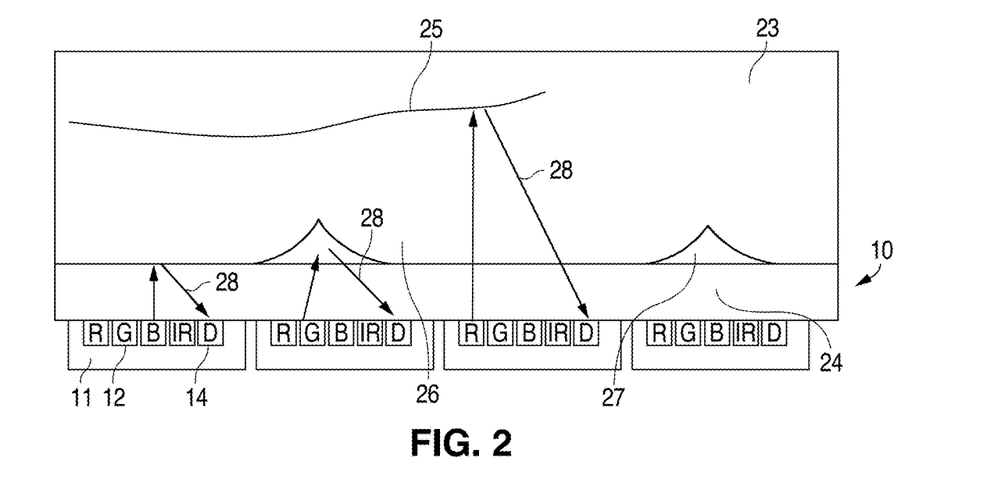
FIG. 2 is a cross-sectional view of the device of FIG. 1 showing a person's finger placed on the light emitting surface for detecting a fingerprint, blood flow, hemoglobin in the blood, or other characteristic for authentication or medical diagnosis.

FIG. 2 is a simplified cross-section of the device 10 of FIG. 1 showing a person's finger 23 in direct contact with a protective glass cover 24 of the device. A blood vessel 25 in the finger 23 is also shown. Due to the finger 23 having an index of refraction (e.g., 1.5) much higher than that of air, yet similar to the index of the glass cover 24, the fingerprint ridges 26 (directly contacting the glass) and the fingerprint valleys 27 (separated from the glass) will cause different amounts of light reflection 28 in those areas. The valley areas will reflect a relatively high percentage of light from the glass surface due to TIR at the glass/air interface, while the ridge areas will absorb a relatively high percentage of the light. Due to the high resolution of the photodiodes 14, some photodiodes 14 will be located under the valleys 27 and others will be located under the ridges 26, so the image of the fingerprint is detectable by the processor 22 (FIG. 1) and can be correlated with a stored fingerprint for authentication of the user.

The glass cover 24 may comprise an inorganic glass, a crystalline material such as sapphire, a glass ceramic, or a polymer.

Ways are known to thwart fingerprint detectors. As an added assurance against fraud, the processor 22 also processes the photodiode 14 data to determine patterns of low wavelength (e.g., red, IR) absorption consistent with blood vessels in the finger. The shape and locations of blood vessels relative to a finger print are unique among individuals and is very difficult to fake. Such data is correlated to stored data for authentication. Other blood data may also be obtained for medical analysis. FIG. 2 shows the light reflectance 28 at the skin depth of the blood vessel 25, where the absorption of red/IR light is higher at the location of a blood vessel compared to areas of the finger not including a blood vessel. A map of the detected blood vessels can then be made by the processor 22 and compared to a stored map of reference blood vessels.

The photodiode 14 signals may be subtracted from each other by the processor 22 so that the differences correlate to absorption of the wavelength of interest. The differences in the signals output by the high resolution photodiodes 14, rather than just their absolute values, allow common-mode rejection of the light directly received by the photodiodes 14 from the LEDs, thus greatly increasing the signal-to-noise ratio.

Generally, the array of photodiodes 14 across an extended area allows for the device 10 to act as an image capture device for items of appropriate contrast in contact or close proximity to the glass cover 24. Accordingly, in the case that a body part such as a finger, palm, wrist or face is in contact with or in close proximity to the glass cover 24, the device 10 may be used to capture beneficial bio-authentication and bio-metric data such as a fingerprint, shallow sub-dermal bio-authentication data such as a blood vessel pattern, facial and other skin tone information, and the presence of skin resident pathogens.

Further, the pixel array may simply be used to detect the presence and motion of one or more fingers or other body parts in contact with or in close proximity to the glass cover 24, thereby allowing the array to be used to sense a variety of gestures or as a touch screen or simple "button" without the requirement for further dedicated touch sensing arrays, mechanical buttons, or discrete gesture subsystems.

Additionally, by sequencing the LEDs 12 of different colors, spectroscopy of the body part may be performed, yielding optically-gathered biometric data. In the case that the wavelengths penetrate the skin to some extent, sub-dermal biometric data may be obtained. For example, red and green can both be used to detect blood flow, blood vessels, and ascertain heart rate, and the combination of red and infrared of appropriate wavelengths may be used to ascertain blood oxygenation.

Different wavelengths penetrate the skin by different amounts; shorter wavelengths (blue, green) penetrating less deeply into the skin than longer wavelengths (red, infrared). Accordingly, by scanning across the pixel wavelengths, images sampling different depths of the dermis may be obtained. The data from the different images may then be subtracted from each other to yield additional resolution. For example, a blue image capturing superficial data may be subtracted from a red image capturing both superficial and sub-dermal data so as to reveal only sub-dermal data.

Extending the range of wavelength response allows even more information to be gathered. By mixing or adding additional pixels with responsivity in either higher or lower frequencies, additional functions such as pathogen detection, UV exposure, hydration, and body chemistry can be ascertained. In some cases, UV may be used to detect fluorescent components in the blood or skin.

Additionally, by capturing a sequence of images (i.e., a video), the migration of pulses of blood along a vessel can be obtained, providing further biometric data such as heart rate, blood pulse wave velocity from which blood pressure may be inferred, cardiac output, stroke volume—either directly, or by inference. The sequence of images may also be used to observe blood flow and to deduce that the body part being examined truly comprises a live body part and does not comprise an attempt to fake a bio-authentication event, such as through use of a spoof material sample or a detached or deceased body part. Likewise, the combinatory use of LEDs generating various colors together with the photodetectors can provide, for example, the identification of materials applied to a human finger which possess a copy of a fingerprint but at the same time show physiological validation. This "video" capability can then help thwart finger print spoofing by conformal materials.

In the case of capturing and processing an extended sequence of images, compensation may need to be provided for the motion of the subject during the video capture. In this case, motion of the superficial image captured with, for example, blue, green or other appropriate light source can be used to track the motion of the subject during video capture and can be used to compensate for motion in the captured sub-dermal images captured, for example, with red or infrared light.

Given that light penetrating into the finger is subject to variations in backscatter and reflection based on the structure in the finger, detection of the fingerprint will be best from light which penetrates least into the finger such as blue light. But a fingerprint can likely be read with a broad range of visible and near infrared wavelengths.

Using longer wavelengths, sub-dermal images can be taken. For example, using an illumination wavelength and power which allows penetration of 2-3 mm or more into the dermis will allow light to penetrate to a sub-dermal region in which capillaries and veins can be found. Given that a blood vessel will be coincident with fingerprint ridges and valleys, the image collected from the vessel will likely also be impacted by the presence of the fingerprint ridges and valleys. Accordingly, the presence of the fingerprint ridges and valleys may both enhance the specificity of the layers used for recognition or can be removed from the image of the vessels. In one instantiation where it is desired to remove the fingerprint, a technique of simply subtracting the image of the fingerprint as captured by shorter wavelength light as previously discussed can be deployed. Alternatively, this may be done via image processing, such as by filtering or other techniques having similar impact. The impact of the fingerprint may also be minimized by setting up the detector array such that the focal point of that detector is essentially solely or largely sub-dermal, such as by the inclusion of optics in the system (shown in later figures).

Figure 3:
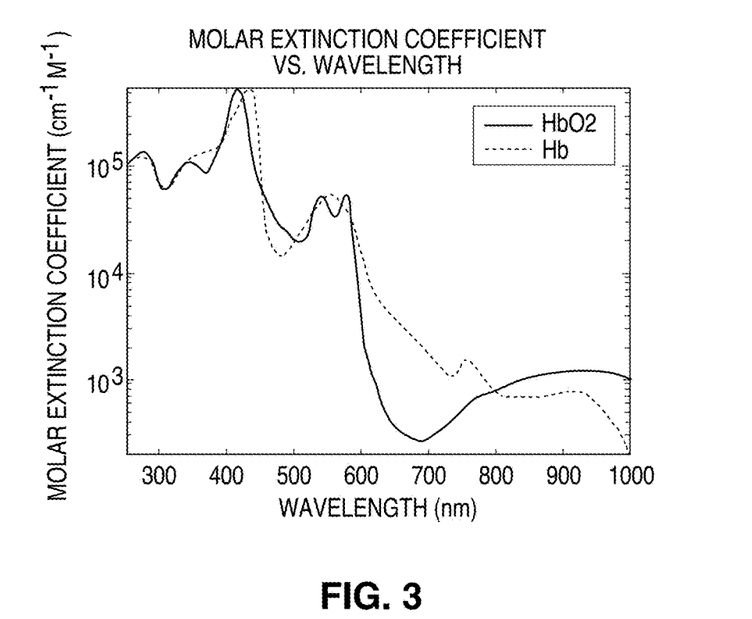
FIG. 3 illustrates a correlation of light wavelengths vs. absorption for hemoglobin and oxy-hemoglobin in the blood, which may be used by a processor in the device of FIGS. 1 and 2 to determine the concentration of such components in the person's blood.

As an artifact of this bio authentication methodology, significant physiological information can simultaneously be extracted. By studying the image of the blood vessels captured under different illuminations, it is possible to perform a spectroscopic analysis of the tissue directly under the sensing area from which the chemistry of the blood, of interstitial fluids, or of tissue can be performed. For example, by studying the image under two different wavelengths such as 680 nm and 850 nm over which hemoglobin and oxy-hemoglobin have different changes in extinction coefficient (FIG. 3), it is possible to get a measure of blood oxygen saturation, SpO2. By extension, by studying images captured under appropriate illumination wavelengths, blood glucose, red blood cell count, white blood cell count, blood CO2, blood glucose, and other blood and interstitial fluid solutes can be detected.

In all of the above configurations, the impact of ambient light may need to be accounted for. Specifically, in the case of studying a thin body part such as a finger, ambient light may propagate through the finger to the detector array, interfering with the received signal or image. Accordingly, the impact of ambient light may need to be accounted for. Ambient light may comprise an essentially steady-state light source such as sunlight or a modulated light source such as incandescent lighting or modulated LED lighting. The portion of the detected optical signal originating from ambient light may be quantified by sampling the detector array first with the array light source in the "off" state. This signal may then be subtracted from the signal that the detector array subsequently captures when the array light sources are in the "on" state so as to deduce the signal relating only to the illumination by the array light source. Additionally, since all the photodiodes 14 may detect the same amount of ambient light, subtracting the common-mode signals cancels out the ambient light.

This method of correlated double sampling can further be enhanced by both the photodetector configuration and the option for multiple photodetectors in each pixel. This "ambient light rejection" can be facilitated by modulating the array light source and array detector sampling times at a frequency much higher than that of any modulation of the ambient light. The frequency of any ambient light modulation may further be detected by the detector array itself.

Whilst the above describes an instantiation utilizing micro-LED displays, a functionally equivalent modality can be achieved through the integration of an extended array of detectors integrated into any other display of appropriate resolution, such as an OLED display or an active-matrix-LCD display. Specifically, if the display includes integrated semiconducting elements such as amorphous silicon, polycrystalline silicon, or organic semiconductors, a photodiode array may be formed on the display using substantially similar semiconducting processing, hence with minimal additional processing cost and higher resolution.

A functionally equivalent modality may also be achieved with a separate extended array of detectors in, for example, an optical module, a chip on glass (a chip attached directly to a cover glass), or a chip on display (a chip attached directly to a display glass). Such a module, chip on glass, or chip on display may be integrated directly with a display, or may comprise a stand-alone array; and may comprise its own illumination sources, or may be arranged so as to utilize external light sources, such as from a display, or any other appropriate existing pixelated, uniform, side, point, or other illumination sources.

Figure 4:
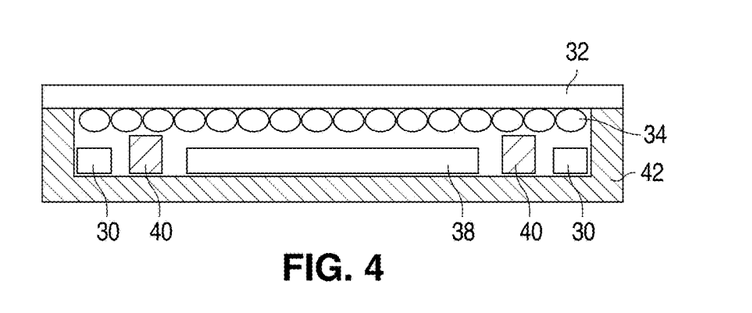
FIG. 4 is a cross-sectional view of another embodiment of a device that includes a light source and photo-sensors for detecting biologic characteristics, where the light is injected into edge portions of a transparent or translucent light guide and emitted from a front surface of the light guide, and where a photo-diode array is positioned behind the light guide for detecting an image of the absorption of light by the person's body.

The extended array of detectors may comprise an integrated sensor array such as a CMOS image sensor, and may have optics integrated as depicted in FIG. 4, described later. The module cover glass itself may optionally be fully or partially coated with optically enhancing, optically filtering, or optically blocking layers, anti-reflection coatings, and the like.

Such a module could operate as an integration point for multiple human interface and physiological enhancements to the end application. Features such as, but not limited to, an optically-functioning on/off or other "button" on consumer devices, gesture recognition for high level functions such as pinch, zoom, scroll, joystick, trackball, signature, for example, can be added to the existing operation via algorithms or software.

An integrated or stand-alone sensor module may also be enhanced with a pressure sensor or pressure-sensing array to provide an additional mechanical button action. A laminated capacitive sensor array layer may also be integrated from which the occurrence of a "touch" event and the associated force of the touch event may be determined. Determination of the force of a touch event may also be used as a feedback to the consumer of a touch event being of a magnitude not optimized to optimal bio-authentication or bio-metric data. For example, pressing too hard on the module may restrict blood flow to the capillaries thereby impacting the signal received therefrom.

An integrated or stand-alone sensor module may further be bonded directly to a display or cover glass via an optically transparent adhesive such as an epoxy, a silicone, an acrylic or a low-temperature melting glass such as a frit glass or compound semiconductor glass. In this case, bonding may comprise an adhesive extending across the entire interface of the module cover glass and the display glass. Alternatively, adhesive may only be dispensed over a portion of the interface (e.g., at the edges), and the majority of the module cover glass and display glass may simply be in contact or close proximity.

FIG. 4 illustrates another embodiment, where the light sources 30, such as LEDs emitting different wavelengths, are located only around the outer edges of a light guide 32, which also serves as the protective cover. The light is coupled into the edge portions of the light guide 32, such as by embedding the LEDs in the light guide 32 or otherwise coupling the light into the edges. The light is carried to all areas of the light guide by TIR and exits through only the top surface of the light guide 32. The light guide 32 may have light extraction features, such as molded micro-reflectors, that direct the light upward and mix the light. Accordingly, the light from the energized LEDs may be substantially uniformly emitted upward into the body part in contact with or proximate to the light guide surface. There is little or no downward light emitted by the light guide 32. Much of the light guide 32 is transparent so that light reflected back from the body part passes through the light guide 32.

Optics 34 may comprise focusing micro-lenses that focus reflected light from only a certain distance into the body part onto a photodiode array 38. The optics 34 may also limit the incoming light from the body part to only a narrow angle normal to the light guide to reduce cross-talk and to better map the features of the body part being analyzed. The photodiode array 38 may be a CMOS image sensor, a CCD image sensor, or any other image sensor.

A light blocking wall 40 may be used to block direct light from impinging on the photodiode array 38. The module may include an opaque heat conductive enclosure 42 to sink heat from the LEDs. The control electronics of FIG. 1 may be attached to the module or separate. The module may have contact pads for soldering to a printed circuit board.

Figure 5:
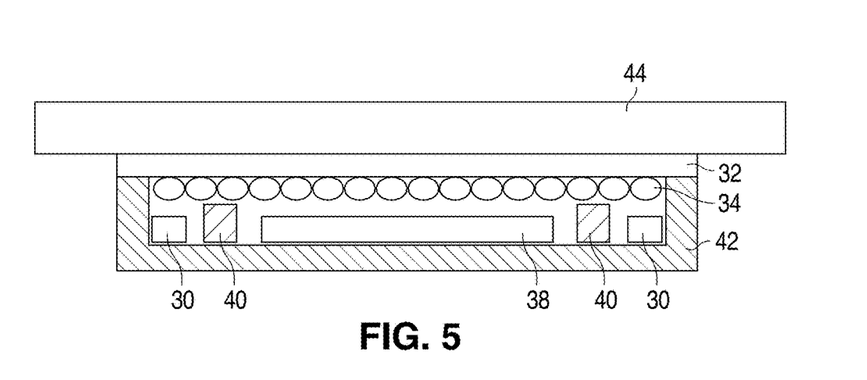
FIG. 5 illustrates the device of FIG. 4 affixed to a transparent layer, such as a protective outer cover portion of a smart phone, laptop computer, or other consumer device.

FIG. 5 illustrates the module of FIG. 4 abutting a protective transparent cover 44, such as a transparent surface layer of a smartphone or other device.

Figure 6:
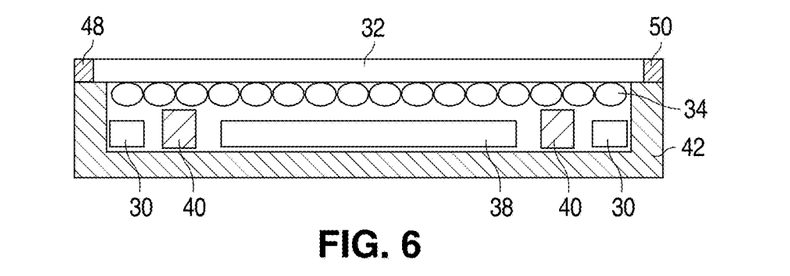
FIG. 6 illustrates the device of FIG. 4 augmented with electrodes for sensing an electrical signal from the person, such as for detection of EKG signals, in combination with detection of the reflected light.

As shown in FIG. 6, an integrated or stand-alone sensor module may further comprise one or more electrodes 48 and 50 extending through or around the light guide 32 or located external to the module but electrically connected to the module to allow a user to be monitored electrically. For example, such electrodes 49 and 50 may be used to detect a user's electrocardiogram (ECG or EKG) or bio-impedance. The ECG signal may be used in isolation to determine heart-rate, or impending or actual medical conditions relating as determined by the form of the ECG signal. Alternatively, the ECG may be used in-tandem with an optically-derived photoplethysmogram (PPG) to determine blood pressure and other medically-important indicators. Bio-impedance may be used to determine hydration, fat content, or other vital signs. Muscular action may also be monitored electrically. All such monitors may combined in a single module.

The ECG signal may also be used as a bio-authentication signature. Thus bio-authentication may be performed via a single modality such as fingerprint, vascular imaging, or ECG; or through a combination of multiple modalities; a form of multi-factor authentication. Given that all bio-authentication events are subject to error in the form of false positives and false negatives, the use of multi-factor bio-authentication can improve the accuracy of bio-authentication. For example, a multi-factor bio-authentication scheme may be configured to confirm an authentication event comprising positive authentication of two factors and rejected authentication of a third factor, thereby reducing the probability of a user being locked-out of a system due to a false negative—albeit at the expense of reduced security—whilst providing increased security against false positives and spoofing by requiring at least two factors to be authenticated. Alternatively, given that different modalities have different authentication times, a multi-factor authentication scheme may be configured to provide a first, fast, low security authentication based on a single, fast authentication factor, and two or more subsequent levels of increasing security authentication over the extended time period required to gather and process the additional slower authentication factors.

Figure 7:
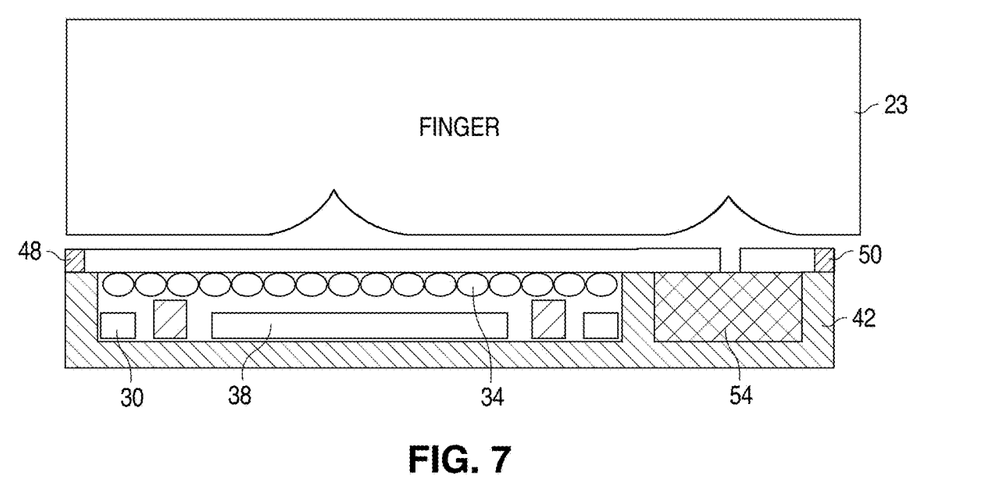
FIG. 7 illustrates the device of FIG. 5 further augmented with a sensitive gas sensing element for detecting gasses emanating from the person.

As shown in FIG. 7, the module may be further augmented with an integrated gas sensing element 54. The gas sensing element 54 may instead be a discrete proximate device. Use of a high-specificity, high-directivity gas sensor, such as an appropriate electrochemical sensing element, may be used to detect current or impeding medical conditions, much as a dog can smell illness in people. Such data can be used in isolation, or in conjunction with the optical and electrical data outlined above to provide a more complete context in which the data can be interpreted, thereby resulting in a more (statistically) accurate medical diagnosis or general health/wellness diagnosis.

Use of a complementary gas sensing element 54 may also be used in a bio-authentication application. A fingerprint spoof sample may comprise fingerprint reproductions into or onto organic materials such as wood, glue, putty, acetate sheets, and the like. Such materials mostly emit volatile organic compounds—especially in the short time after formation or curing. Additionally, humans all emit volatile organic compounds (VOCs) through the skin and sweat. Therefore, a contact or close-proximity fingerprint or other bio-authentication event in which the gaseous environment at the contact point is sampled at substantially the same time as the bio-authentication event has the opportunity to "smell" the presence of a spoof material or direct skin. Further, the particular ratios of VOCs emitted by any one individual (one's "odor") may be sufficiently distinct that it may be used as a further bio-identification factor or modality if sufficient resolution exists in the gas sensing element. Such a sensing scheme is depicted in FIG. 7 by the photo-diode array 38 sensing light absorption by the fingerprint and/or blood vessel location in conjunction with the gas sensing element 54 detecting the presence of an actual human finger 23.

An integrated or stand-alone sensor module may be arranged as a compact line-scanner (single or narrow line of pixels) across which a finger can be physically scanned or swiped. This may provide the advantage of being able to scan an extended part of the finger or other body part with a reduced sensor footprint. In the case of a stand-alone sensor module, the reduced footprint can facilitate design-in to space constrained platforms such as cellphones, watches and other wearables and can facilitate reduced module cost. The swiping action of the finger can allow the small form factor sensor to survey an extended range of body tissue. Being able to sense over extended ranges of body tissue provides the advantage that particular bio-authentication and bio-metric markers can be sampled in the specific tissue areas where the markers are the strongest or most highly defined. For example, if trying to obtain a traditional fingerprint, scanning tissue over the distal phalanges will provide the most useful information since that is a region rich in superficial skin features (ridges and valleys). On the other hand, capturing unique sub-dermal information such as finger vein identification data may prove most successful over the middle phalanges where the veins are larger, hence both easier to detect and less impacted by the application of pressure to the finger by contact with the sensor module during the bio-authentication event. Accordingly, an optical bio-authentication line scanner may be configured to optimally capture fingerprint data from the distal phalange and finger vein identification data from the middle phalange as the finger is scanned over it. The module may further sense the passage of the finger over the module and change the operation of the module during the finger scan, such as by a change in illumination source or focal length as the sensor passes under one of the interphalangeal joints.

A line array sensor may further be formed on or behind a flat cover glass, or a curved cover glass, the curve of the glass approximately matching that of the finger or a wrist. Such a sensor may then be incorporated into a wearable device such as a ring or a watch which, if networked, can be used to as a wearable device providing bio-authentication of the user. Such a device can perform a one-time bio-authentication event. It can then continuously or periodically pole the sensor array to confirm that the wearable device has not been removed and that the user is still alive. The wearable device can then confirm that the user remains bio-authenticated without having to perform any subsequent bio-authentication events. Such a device can then be wirelessly networked, for example, with phones, credit card payment systems, ATMs, cars, doors, data vaults and the like to facilitate fast user authentication. Such a modality is of particular use in the case that a bio-authentication event comprises a lengthy event, such as if it comprises an analysis of ECG signals which may require several heart beats to be captured.

Figure 8:
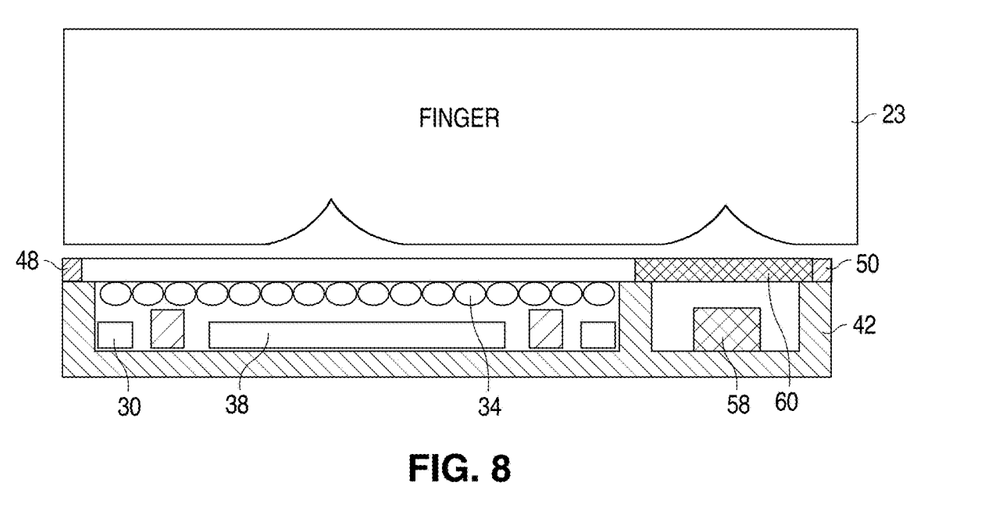
FIG. 8 illustrates the device of FIG. 5 further augmented with a non-contact, infra-red temperature sensor for determining the temperature of the body part (e.g., a finger) in contact with the device.

As shown in FIG. 8, signals from an integrated or stand-alone sensor module may be further augmented with data from an integrated or discrete proximate contact or non-contact temperature sensor 58. A low wavelength (red or IR) filter 60 may cover the sensor 58. Temperature data may be used as a standalone biometric or may be used to provide further context within which other biometrics are interpreted.

Figure 9:
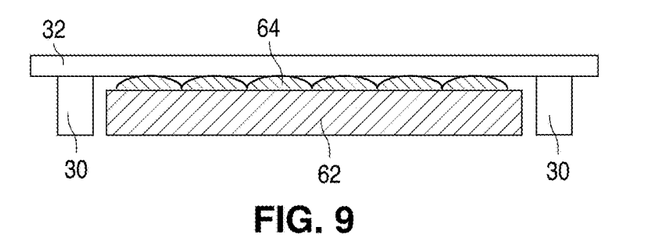
FIG. 9 illustrates another embodiment of the invention where focusing lenses are abutting the photosensor array for higher resolution, for a higher signal-to-noise ratio, and for forming a more compact device.

FIG. 9 shows an embodiment where the control circuitry and photodiodes are integrated in a sensor chip 62, and the focusing optics 64 is formed directly on the photodiode array for more precise focusing. The focusing may be within a certain distance into the body part contacting the light guide 32. The edge-coupled LED light sources 30 are also shown. The resulting module is very thin and easily incorporated into various applications.

Figure 10:
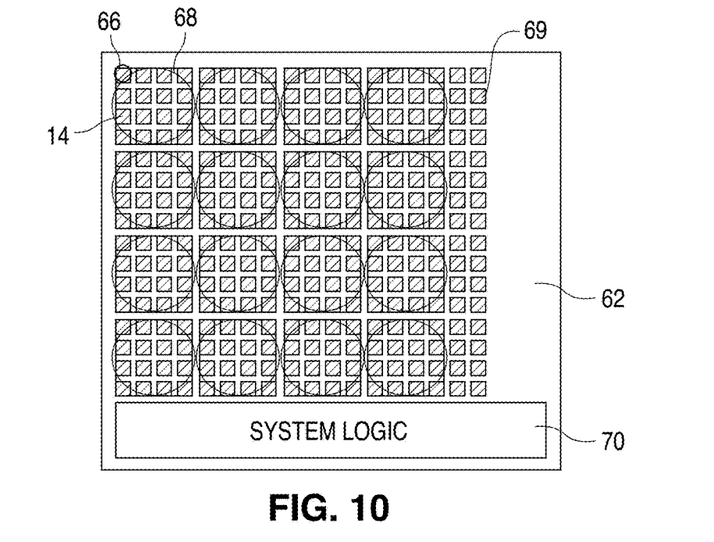
FIG. 10 is a front view of a single integrated circuit chip having a high resolution array of photodetectors. A lens array is positioned over the detector array, which focuses the incoming light and which reduces the amount of direct light entering the photo-detectors for increasing the signal-to-noise ratio. A light source may have many suitable designs, such as a transparent light guide that emits light only in the direction of a person's body part in contact with the light guide. Reflected light is transmitted back through the light guide to the photodetectors.

FIG. 10 is a top down view of one embodiment of the sensor chip 62 and optics of FIG. 9. Each photodiode 14 may be less than 0.25 mm$^2$ to form a compact array. A separate micro-lens 66 is formed over each photodiode 14 to improve light capture. Larger plenoptic lenses 68 are formed over sections of the photodiode array, where each plenoptic lens 68 may overlap about 16 photodiodes 14. The plenoptic lenses 68 may focus at different depths and be directional to gather more information about the reflected light from the body part. The various lenses may be formed by molding a transparent sheet and laminating the sheet over the photodiode array, or may be formed by direct molding over the photodiode array. Although hemispherical lenses are shown for simplicity, the lenses may be any shape suitable for focusing. The chip can be affixed to the back of any light guide glass. In another embodiment, the optics is spaced from the photodiode array with a spacer. Reference photodiodes 69 may be located outside of the plenoptic lenses 68 for detecting ambient light. System logic 70, for processing the detected signals, is formed on the same chip as the photo-diode array for compactness and improving the signal-to-noise ratio. The logic may include analog-to-digital converters and digital processing circuitry.

Figure 11:
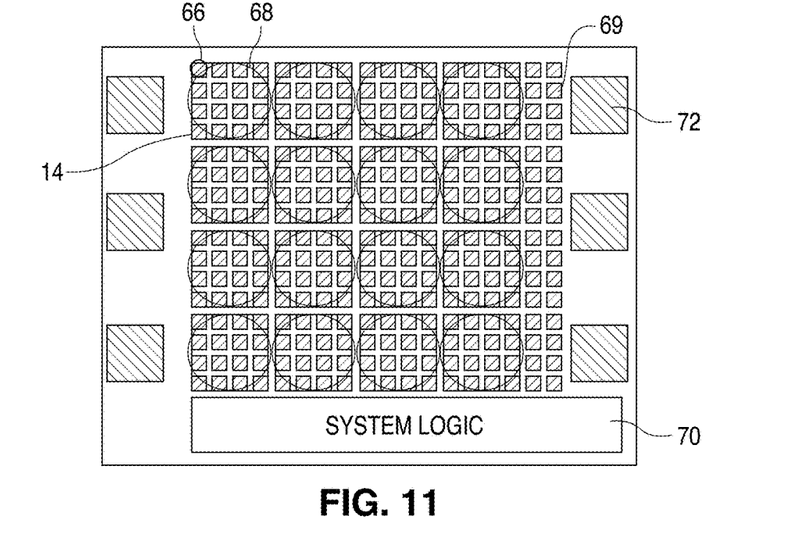
FIG. 11 is similar to FIG. 10 but integrates the light sources (e.g., LEDs or lasers) on the same surface as the photodetectors.

FIG. 11 illustrates the module of FIG. 10 augmented with LED light sources 72. The light sources 72 may inject light into an overlying light guide to spread the light over the photodiode array. Light reflecting from the body part passes back through the light guide to the photodiode array. In another embodiment, a light guide is not needed since the module may be small (e.g., less than 2×2 cm) and the light from the LEDs light sources 72 is scattered within the body part and reflected onto the photodiode array.

Since LED performance degrades over time, the photodiodes 14 may also be used to compare the LED light output against a baseline and provide feedback to the LED energizing circuitry to achieve the baseline performance.

Although the embodiments above comprise spectroscopic analysis performed by an array of broad-band detectors in conjunction with narrowband emitters, the functionality could also be implemented through the use of wavelength-specific detectors such as detectors with optical filters on them or in their optical path, in conjunction with broadband emitters such as phosphor-converted white-LEDs.

Figure 12:
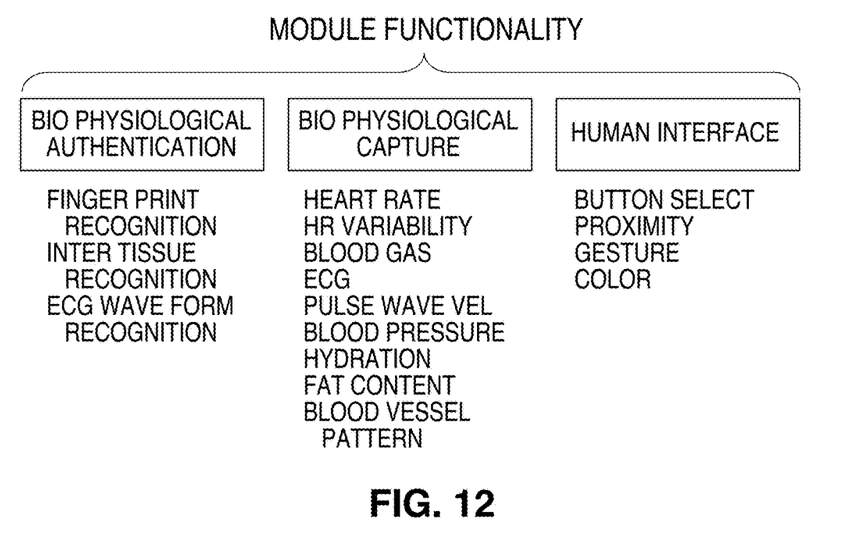
FIG. 12 identifies functions that may be performed with the various devices.

FIG. 12 identifies various possible uses of the modules described herein.

Figure 13:
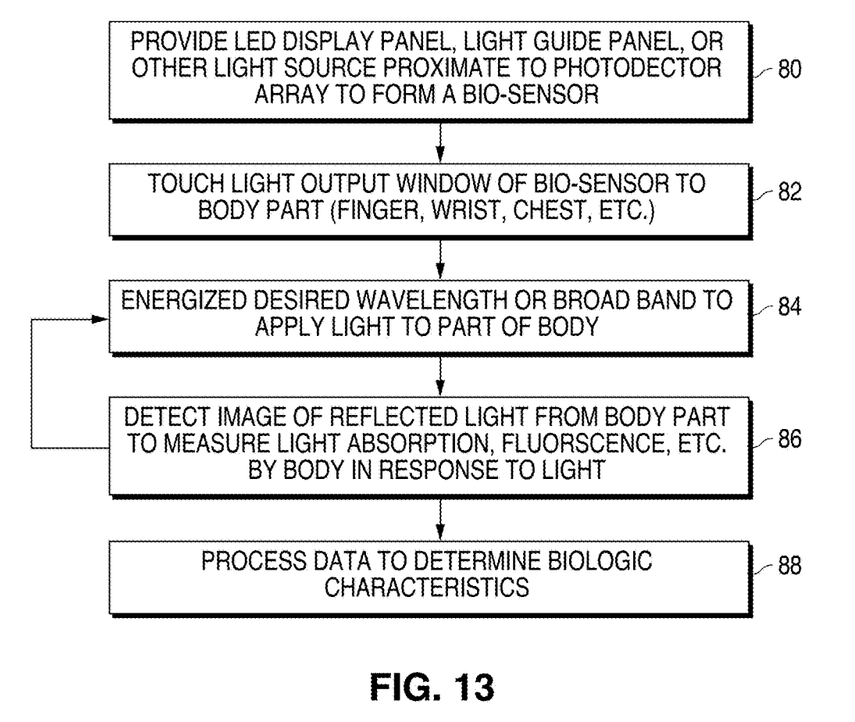
FIG. 13 is a flowchart of an example of basic steps performed by the device to detect biologic characteristics of the user.

FIG. 13 is a flowchart identifying basic steps performed by the various modules according to one embodiment of the invention.

In step 80, an LED display panel, light guide panel, or other light source is arranged relative to a photodetector array to form the bio-sensor.

In step 82, the output window of the bio-sensor is touched by a body part for analysis. A touch sensor, or a light shadow sensor, may be incorporated in the device for detecting when a body part is over the output window to start the image detection process.

In step 84, the LEDs are energized to apply the desired wavelengths to the body part to detect localized light absorption by the body part for fingerprint detection, blood vessel detection, pulse, etc. The LEDs may be energized concurrently or sequentially. If the LEDs are energized sequentially, the photodetectors may be selectively read so as to better associate absorption of the light with the locations in the body part proximate to the energized LED. The sequential illumination may be in any pattern.

In step 86, the signals from the photodetector array are scanned, such as by column and row, to detect the relative magnitudes of the detected light across the array to effectively obtain a detailed image of the light absorption by the body part.

In the event that the LEDs are sequentially energized, the method may then loop back to step 84 after each energization to provide additional spatial absorption data.

In step 88, the raw data is processed by the module's processor to obtain results, such as authentication of the user, medical analysis, etc.

While particular embodiments of the present invention have been shown and described, it will be obvious to those skilled in the art that changes and modifications may be made without departing from this invention in its broader aspects and, therefore, the appended claims are to encompass within their scope all such changes and modifications that are within the true spirit and scope of this invention.

What is claimed is:

1. A bio-sensor device comprising:
    a first surface;
    a plurality of light sources controllable to generate a variable spectrum of light containing a first peak wavelength for penetrating a person's finger touching the first surface to detect a blood-related biological characteristic in the finger, and containing a second peak wavelength for detecting the person's fingerprint while touching the first surface;
    an array of photodetectors arranged to detect the light of the variable spectrum reflected back by at least the finger, through the first surface, the photodetectors generating first signals corresponding to the light reflected back;
    wherein the plurality of light sources comprises a two-dimensional pixel array containing light emitting diodes emitting at least the first peak wavelength and the second peak wavelength, wherein the pixel array is configured to display a full color image using red, green, and blue subpixels,
    wherein the red subpixels emit light of the first peak wavelength, and the light of the second peak wavelength is emitted by other ones of the subpixels,
    wherein the photodetectors are distributed within the pixel array;
    a controller configured to energize one or more of the red subpixels, during a first time period, to cause the light of the first peak wavelength to penetrate the person's finger to detect the blood-related biological characteristic in the finger, wherein reflected light from the one or more red subpixels is detected by the photodetectors to generate the first signals conveying information about the blood-related biological characteristic in the finger,
    the controller also configured to energize other ones of the subpixels, during a second time period different from the first time period, to cause the light of the second peak wavelength to reflect off the person's finger to detect the person's fingerprint, wherein reflected light from the other ones of the subpixels is detected by the photodetectors to generate the first signals conveying information about the person's fingerprint; and
    detection circuitry coupled to the array of photodetectors configured for analyzing the first signals to determine the blood-related biological characteristic in the person's finger and the person's fingerprint.

2. The device of claim 1 wherein individual ones of the photodetectors are associated with individual ones of the light emitting diodes.

3. The device of claim 1 wherein each pixel includes at least one light emitting diode and a photodetector.

4. The device of claim 3 wherein there are a plurality of light emitting diodes within each pixel, and wherein each light emitting diode within a pixel emits a different peak wavelength of light.

5. The device of claim 1 further comprising lenses over the photodetectors configured for limiting an angular range of reflected light from the finger to reduce cross-talk between the photodetectors, wherein the lenses over the photodetectors are further configured for focusing reflected light from the finger onto the photodetectors from only a certain distance into the finger.

6. The device of claim 1 further comprising a non-optical sensor integrated into the device.

7. The device of claim 6 wherein the non-optical sensor comprises electrodes for touching by the finger.

8. The device of claim 6 wherein the non-optical sensor comprises a gas sensor for sensing at least one gas emitted by the finger.

9. The device of claim 1 further comprising a processor integrated into the device, the processor controlling energization of the light source and detection of the reflected light received by the photodetectors.

10. The device of claim 1 further comprising a processor, the processor being configured to process data from the photodetectors, compare the data to stored data, and indicate authentication of a user of the device.

11. The device of claim 1 further comprising a processor configured to control the light emitting diodes to be sequentially illuminated while signals from one or more of the photodetectors are read and processed by the processor.

12. The device of claim 1 further comprising a processor, wherein the processor is configured to detect a light reflection image internal to the finger to determine areas of absorption of the light internal to the finger.

13. The device of claim 1 further comprising a processor configured to process data from the photodetectors, wherein the processor detects movement of the finger for detecting a gesture.

14. The device of claim 1 wherein the blood-related biological characteristic comprises at least one of a heart rate and blood flow in the finger.

15. The device of claim 1 wherein the blood-related biological characteristic comprises a location of a blood vessel in the finger.

16. The device of claim 1 further comprising infra-red emitting light emitting diodes (LEDs) distributed within the pixel array, but not contributing to the full color image, where the infra-red emitting LEDs are controllable for detecting characteristics of blood within the finger.

* * * * *